United States Patent
Coffman et al.

(10) Patent No.: US 6,933,370 B2
(45) Date of Patent: Aug. 23, 2005

(54) METHODS FOR PURIFYING HIGHLY ANIONIC PROTEINS

(75) Inventors: Jonathan L. Coffman, Haverhill, MA (US); William Barry Foster, Chelmsford, MA (US); Bonnie J. Germain, Webster, NH (US); Shujun Sun, Brentwood, NH (US); Jeffrey J. Robinson, Amesbury, MA (US)

(73) Assignee: Genetics Institute, LLC, Cambridge, MA (US)

( * ) Notice: Subject to any disclaimer, the term of this patent is extended or adjusted under 35 U.S.C. 154(b) by 302 days.

(21) Appl. No.: 09/819,157

(22) Filed: Mar. 27, 2001

(65) Prior Publication Data

US 2002/0132991 A1 Sep. 19, 2002

Related U.S. Application Data

(60) Provisional application No. 60/193,351, filed on Mar. 27, 2000.

(51) Int. Cl.$^7$ .............................. A23J 1/00; C07K 1/00
(52) U.S. Cl. ...................................... 530/412; 530/350
(58) Field of Search .................... 435/69.1, 6; 530/412, 530/350, 300, 395, 387.1; 514/2

(56) References Cited

U.S. PATENT DOCUMENTS

| | | | | |
|---|---|---|---|---|
| 5,034,133 A | * | 7/1991 | Naveh et al. ................ 210/635 |
| 5,115,101 A | | 5/1992 | Bloom et al. .......... 530/388.25 |
| 5,429,746 A | | 7/1995 | Shadle et al. ............... 210/635 |
| 5,827,817 A | | 10/1998 | Larsen et al. .................. 514/2 |
| 5,852,175 A | | 12/1998 | Cummings et al. .... 530/388.73 |
| 6,005,075 A | | 12/1999 | Ettlin et al. ................. 530/351 |
| 6,005,081 A | | 12/1999 | Burton et al. ............... 530/399 |
| 6,005,082 A | | 12/1999 | Smeds ........................ 530/417 |
| 6,008,036 A | | 12/1999 | Fanget et al. ............... 435/239 |
| 6,008,328 A | | 12/1999 | Hsu et al. .................... 530/412 |
| 6,028,191 A | | 2/2000 | Nardella et al. ............. 536/124 |
| 6,423,831 B1 | * | 7/2002 | Burton et al. ............... 530/399 |

OTHER PUBLICATIONS

Scopes RK. Protein purification : principles and practice 2nd ed. New York : Springer–Verlag, c1987.*

Li, F. et al., "Visualization of P–selectin glycoprotein ligand–1 as a highly extended molecule and mapping of protein epitopes for monoclonal antibodies," *J. Biol. Chem.* Mar. 15, 1996;271(11):6342–8.

Moore, K.L. et al., "The P–selectin glycoprotein ligand from human neutrophils displays sialylated, fucosylated, O–linked poly–N–acetyllactosamine," *J. Biol. Chem.* Sep. 16, 1994;269(37):23318–27.

* cited by examiner

*Primary Examiner*—Jon Weber
*Assistant Examiner*—Sheridan K Snedden
(74) *Attorney, Agent, or Firm*—Fitzpatrick, Cella, Harper & Scinto

(57) ABSTRACT

The present invention provides a process for isolating and purifying highly anionic target proteins, for example, sulfated proteins. Sulfated proteins have five (5) or more, sulfations. In a preferred embodiment, the sulfated protein has six (6) sulfations, e.g., six sulfations on N-terminal tyrosine residues, as embodied in PSGL-1 (P-selectin glycoprotein ligand).

13 Claims, 9 Drawing Sheets

SEQUENCE LISTING

<160> NUMBER OF SEQ ID NOS: 1

<210> SEQ ID NO 1
<211> LENGTH: 402
<212> TYPE: PRT
<213> ORGANISM: Homo Sapiens

<400> SEQUENCE: 1

```
Met Pro Leu Gln Leu Leu Leu Leu Ile Leu Leu Gly Pro Gly Asn
 1               5                  10                  15

Ser Leu Gln Leu Trp Asp Thr Trp Ala Asp Glu Ala Glu Lys Ala Leu
                20                  25                  30

Gly Pro Leu Leu Ala Arg Asp Arg Arg Gln Ala Thr Glu Tyr Glu Tyr
            35                  40                  45

Leu Asp Tyr Asp Phe Leu Pro Glu Thr Glu Pro Pro Glu Met Leu Arg
        50                  55                  60

Asn Ser Thr Asp Thr Thr Pro Leu Thr Gly Pro Gly Thr Pro Glu Ser
 65                  70                  75                  80

Thr Thr Val Glu Pro Ala Ala Arg Arg Ser Thr Gly Leu Asp Ala Gly
                85                  90                  95

Gly Ala Val Thr Glu Leu Thr Thr Glu Leu Ala Asn Met Gly Asn Leu
            100                 105                 110

Ser Thr Asp Ser Ala Ala Met Glu Ile Gln Thr Thr Gln Pro Ala Ala
        115                 120                 125

Thr Glu Ala Gln Thr Thr Pro Leu Ala Ala Thr Glu Ala Gln Thr Thr
    130                 135                 140

Arg Leu Thr Ala Thr Glu Ala Gln Thr Thr Pro Leu Ala Ala Thr Glu
145                 150                 155                 160

Ala Gln Thr Thr Pro Pro Ala Ala Thr Glu Ala Gln Thr Thr Gln Pro
                165                 170                 175

Thr Gly Leu Glu Ala Gln Thr Thr Ala Pro Ala Ala Met Glu Ala Gln
            180                 185                 190

Thr Thr Ala Pro Ala Ala Met Glu Ala Gln Thr Thr Pro Pro Ala Ala
        195                 200                 205

Met Glu Ala Gln Thr Thr Gln Thr Thr Ala Met Glu Ala Gln Thr Thr
    210                 215                 220

Ala Pro Glu Ala Thr Glu Ala Gln Thr Thr Gln Pro Thr Ala Thr Glu
```

-continued

```
            225                 230                 235                 240
Ala Gln Thr Thr Pro Leu Ala Ala Met Glu Ala Leu Ser Thr Glu Pro
                245                 250                 255

Ser Ala Thr Glu Ala Leu Ser Met Glu Pro Thr Thr Lys Arg Gly Leu
            260                 265                 270

Phe Ile Pro Phe Ser Val Ser Ser Val Thr His Lys Gly Ile Pro Met
        275                 280                 285

Ala Ala Ser Asn Leu Ser Val Asn Tyr Pro Val Gly Ala Pro Asp His
    290                 295                 300

Ile Ser Val Lys Gln Cys Leu Leu Ala Ile Leu Ile Leu Ala Leu Val
305                 310                 315                 320

Ala Thr Ile Phe Phe Val Cys Thr Val Val Leu Ala Val Arg Leu Ser
                325                 330                 335

Arg Lys Gly His Met Tyr Pro Val Arg Asn Tyr Ser Pro Thr Glu Met
                340                 345                 350

Val Cys Ile Ser Ser Leu Leu Pro Asp Gly Gly Glu Gly Pro Ser Ala
            355                 360                 365

Thr Ala Asn Gly Gly Leu Ser Lys Ala Lys Ser Pro Gly Leu Thr Pro
    370                 375                 380

Glu Pro Arg Glu Asp Arg Glu Gly Asp Asp Leu Thr Leu His Ser Phe
385                 390                 395                 400

Leu Pro
```

METHODS FOR PURIFYING HIGHLY ANIONIC PROTEINS

RELATED APPLICATIONS

This application claims the benefit of prior-filed provisional patent application Ser. No. 60/193,351, filed Mar. 27, 2000, entitled "METHODS FOR PURIFYING HIGHLY ANIONIC PROTEINS". The entire content of the above-referenced application is incorporated herein by this reference.

BACKGROUND OF THE INVENTION

Purification of target proteins is often encumbered by poor DNA removal due to DNA/protein interactions. DNA/protein interactions are more problematic in the purification of highly anionic target proteins, e.g., sulfated proteins.

SUMMARY OF THE INVENTION

The present invention provides methods for isolating and purifying highly anionic target proteins and target proteins comprising immunoglobulin domains, for example, sulfated proteins. Anionic proteins are proteins which have a net negative charge. Sulfated proteins are proteins in which the net negative charge is due to at least about one (1) sulfated residue. Sulfation of a target protein refers to the substitution of at least one hydroxyl group (—OH) with —$SO_4H$ on or between amino acid(s) contained within the target protein. In a preferred embodiment, the sulfated protein has at least about one (1) sulfate group. Sulfated proteins containing at least about two (2), three (3), four (4), five (5), six (6) or more sulfate groups are also encompassed by the present methods, e.g., six sulfate groups on the N-terminal tyrosines as embodied in PSGL-1 (P-Selectin Glycoprotein Ligand-1).

In one aspect, the invention provides a method for purifying highly anionic target proteins comprising the steps of ion exchange chromatography under appropriate conditions for the purification of the target proteins. For example, this method provides for (1) contacting the sample with a substrate capable of reversibly binding charged molecules whereby the target proteins bind to the substrate, (2) washing the substrate with a first wash solution under appropriate conditions whereby a plurality of proteinaceous and non-proteinaceous impurities in the sample either do not bind or are washed off the substrate while the highly anionic target proteins remain bound, (3) eluting the sample with a first elution solution wherein the first elution solution comprises a salt solution at a high molar concentration, and (4) collecting the eluted sample containing the purified anionic target proteins.

In one embodiment, the pH of the first wash solution is about 4.0 to 8.0. In another embodiment, the pH of the first wash solution is about 6.5.

In a preferred embodiment the highly anionic target protein is a sulfated protein and the impurities include a sulfated form of the target protein.

In another aspect, the eluted sample from the ion exchange chromatography purification which contains the purified target proteins can be further purified. This further purification, for example, comprises the steps of hydrophobic interaction and/or metal chelate chromatography under appropriate conditions for the purification of the highly anionic target proteins. For example, this further purification provides for the steps of (1) passing the eluted sample containing the target proteins through a metal chelate chromatography column or a hydrophobic interaction chromatography column whereby the eluted sample is captured on the column, (2) washing the column with a second wash solution under appropriate conditions whereby DNA/histone complexes contained in the sample are dissociated, (3) eluting the sample with a second elution solution, and (4) collecting the eluted sample containing the purified highly anionic target proteins.

In one embodiment, the second wash solution comprises a high salt concentration and the second elution solution comprises a lower salt concentration than the second wash solution. For example, under hydrophobic interaction chromatographic conditions, the concentration of the salt in the second wash solution is about 4M, and the concentration of the salt in the second elution solution is about 0.48M. Alternatively, under hydrophobic interaction chromatographic the second wash solution is selected from the group consisting of (a) a solution comprising NaCl at about 4M and Tris at about 20 mM and a pH of about 7.4, (b) a solution comprising isopropanol at about 5% and ammonium sulfate at about 1.2M, (c) a solution of ethanol at about 5% and ammonium sulfate at about 1.2M, and (d) a solution of ethanol of about 5% and NaCl at about 4M.

Under iron chelation chromatographic conditions, for example, the second wash solution comprises a salt concentration of about 2M, and the second elution solution comprises a salt concentration of about 200 mM to 1M. Alternatively, under iron chelation chromatographic conditions, the second wash solution comprises MES at about 40 mM, NaCl at about 2M, and imidazole at about 5 mM, and the second elution solution comprises a solution of MES at about 40 mM, NaCl at about 1M, and imidazole at about 35 mM.

In another aspect, the target proteins have at least about one (1) sulfation(s). Anionic target proteins having at least about two (2), three (3), four (4), five (5), six (6), or more sulfations are also encompassed by the present invention, e.g., PSGL-1 proteins. Anionic proteins capable of being purified by the present invention can be naturally occurring or recombinant proteins.

In another aspect, the invention provides a method for the purification of highly anionic proteins comprising an immunoglobulin domain (e.g., an immunoglobulin Fc domain), for example, a PSGL-Ig fusion protein. This method comprises the steps of (1) contacting the sample with a substrate capable of binding the Fc portion of the target protein comprising an immunoglobulin domain whereby the target molecules bind to the substrate, (2) washing the substrate with a first wash solution under appropriate conditions to wash away contaminants contained in the sample, (3) eluting the sample with a first elution solution wherein the pH of the first elution solution is low, e.g., about 4.0, preferably about 3.7, and (4) collecting the eluted sample containing the purified anionic target proteins.

In another embodiment, the eluted sample from the Fc binding substrate which contains the purified highly anionic target proteins comprising an immunoglobulin domain is further purified. For example, further purification comprises the steps of (1) contacting the eluted sample containing the purified anionic target proteins comprising an immunoglobulin domain with a substrate capable of reversibly binding charged molecules whereby a plurality of proteinaceous and non-proteinaceous impurities in the sample either do not bind or are washed off the substrate while the target proteins remain bound to the substrate, (2) washing the substrate with a second wash solution wherein the pH of the second wash solution is low, e.g., about 4.0, preferably about 3.8, (3)

eluting the sample with a second elution solution, and (4) collecting the eluted sample containing the purified anionic target proteins comprising an immunoglobulin domain.

In one aspect, the target proteins comprising an immunoglobulin domain have at least about one (1) sulfation(s). Immunoglobulins comprising proteins with at least two (2), three (3), four (4), five (5), six (6), or more sulfations are also encompassed by the present invention, e.g., PSGL-Ig.

In a preferred embodiment, the purification methods of the invention provide purified highly anionic target proteins and purified highly anionic proteins comprising an immunoglobulin domain (e.g., PSGL-Ig) at least about 99.9% pure of contaminating proteins.

In another embodiment, the purification methods of the invention removes at least about 95% or 2.5 $\log_{10}$ removal value (LRV) of the contaminating DNA from the highly anionic target proteins and the highly anionic proteins comprising an immunoglobulin domain.

Other features and advantages of the invention will be apparent from the following detailed description and claims.

DETAILED DESCRIPTION OF THE INVENTION

Figure 1:
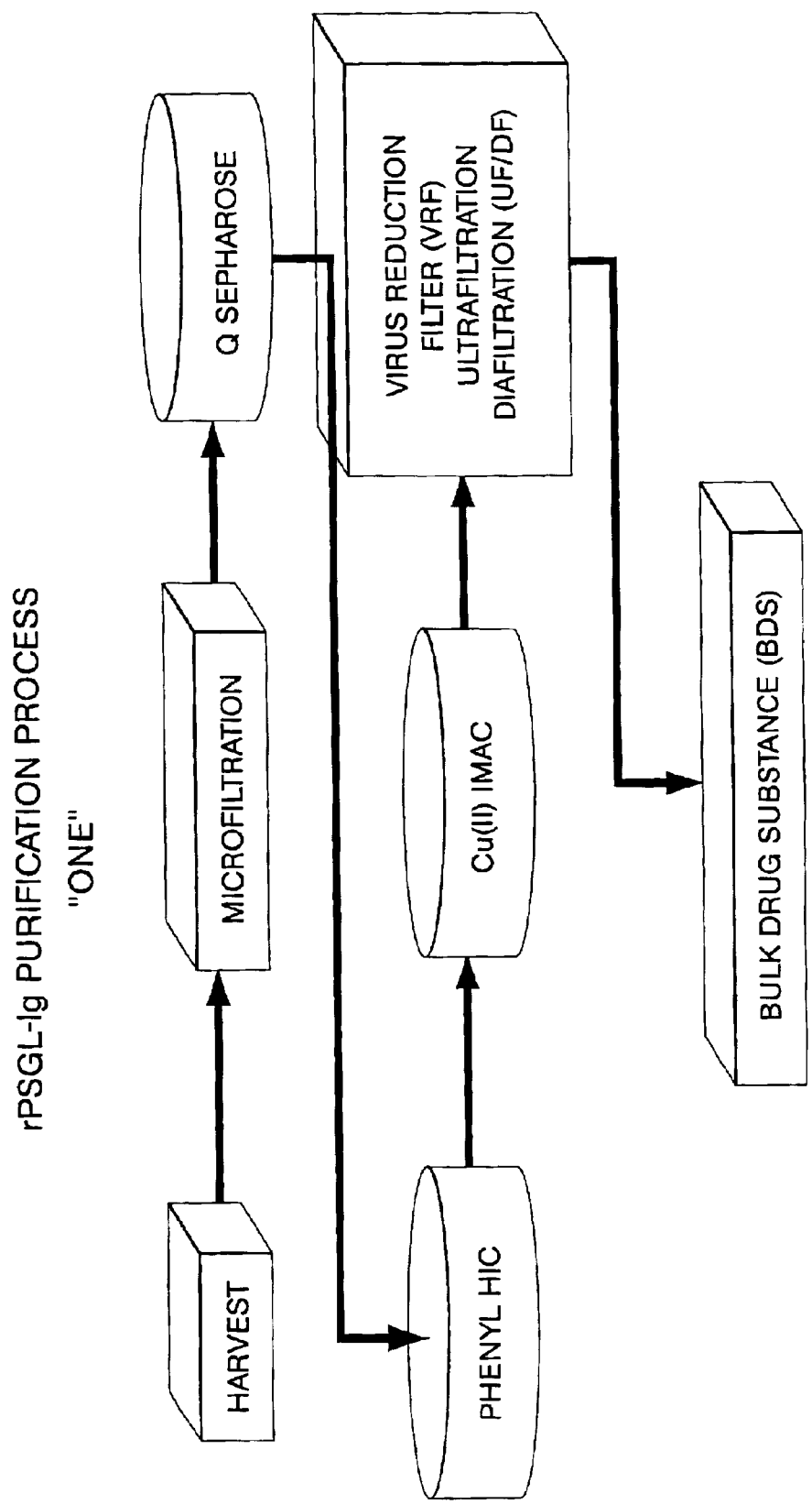
FIGS. 1, 2A–2G and 3 depict the purification methods described herein, e.g., processes I—III, as described in the Examples.
Figure 2A:
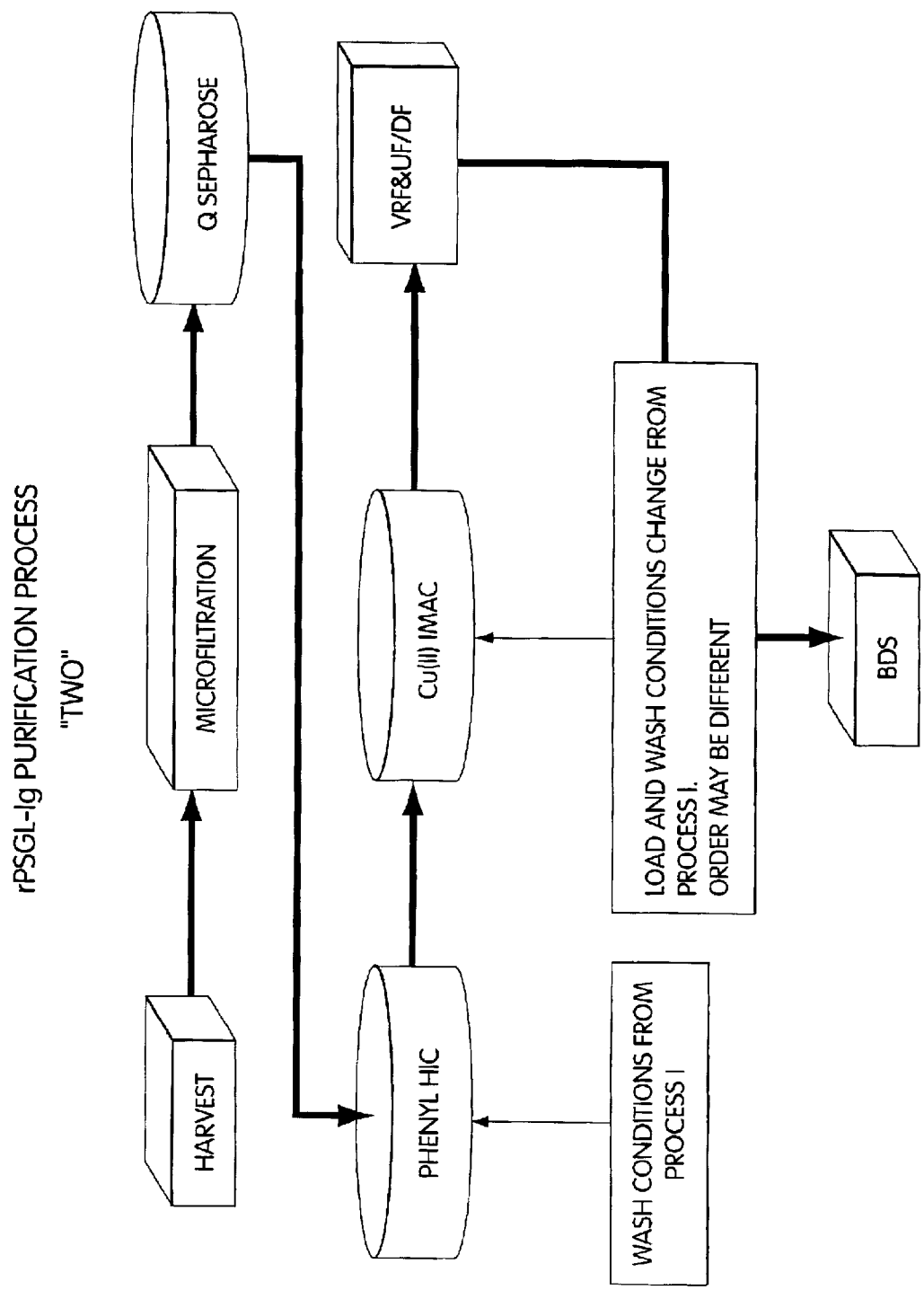
Figure 2B:
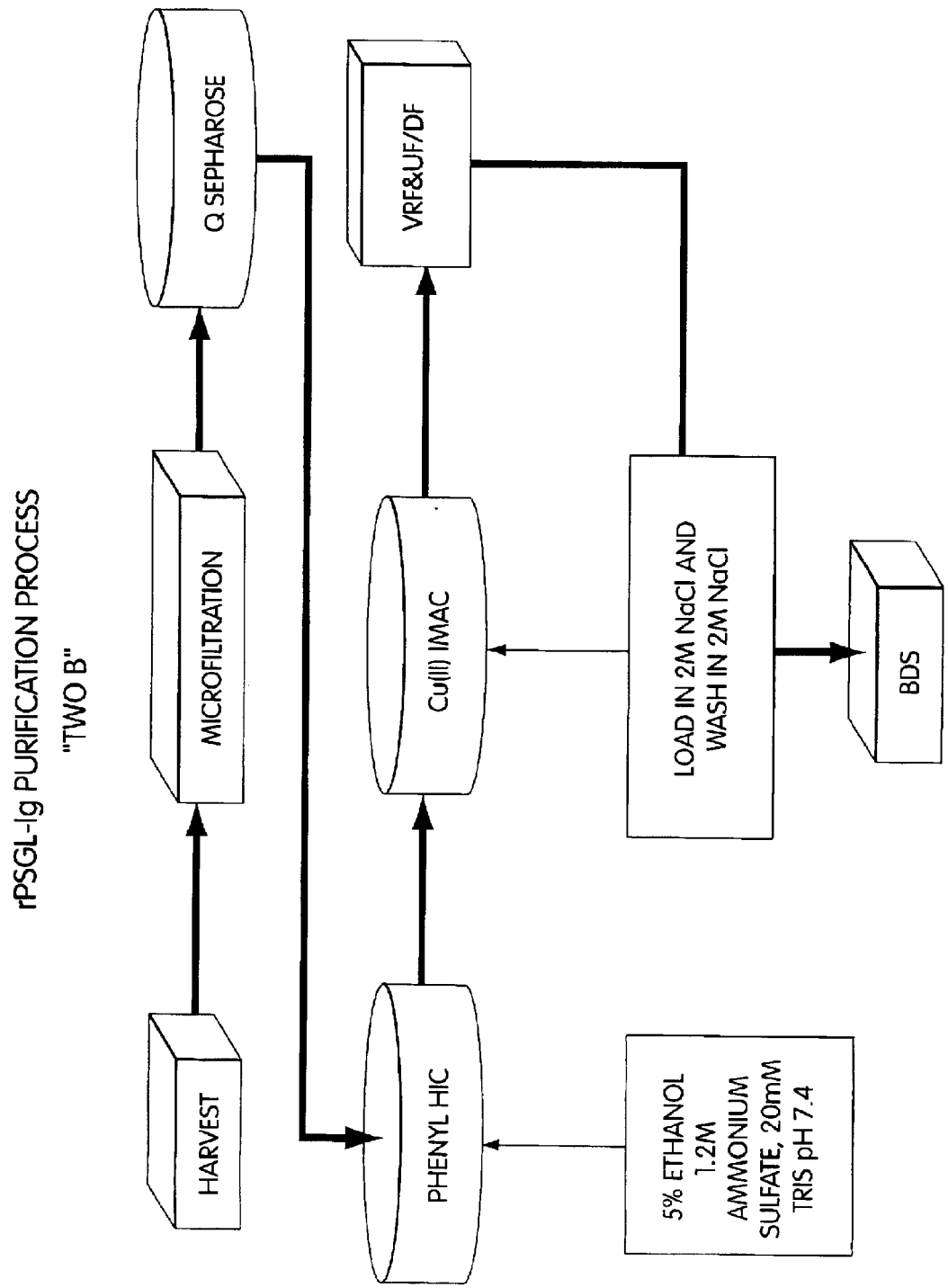
Figure 2C:
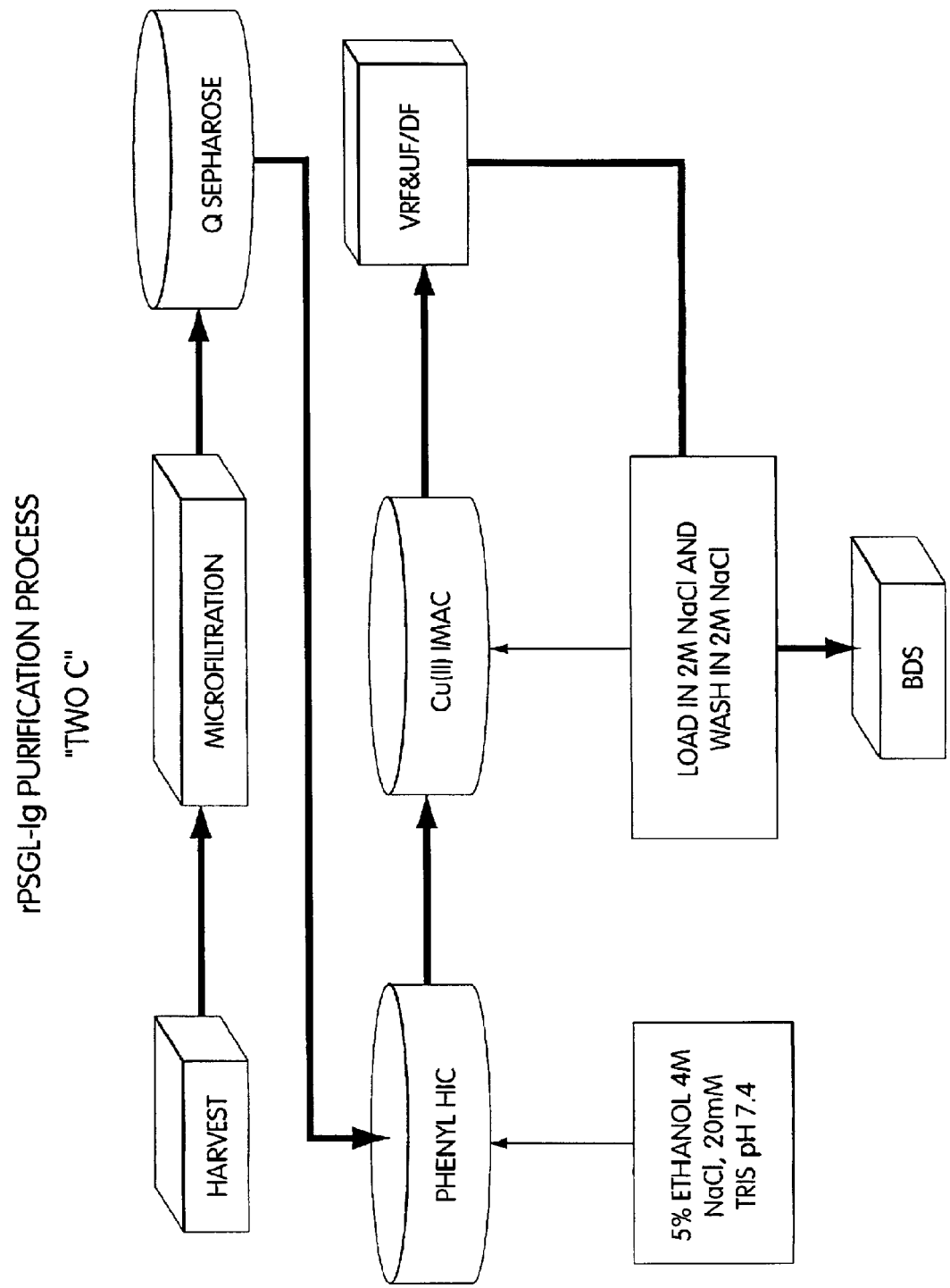
Figure 2D:
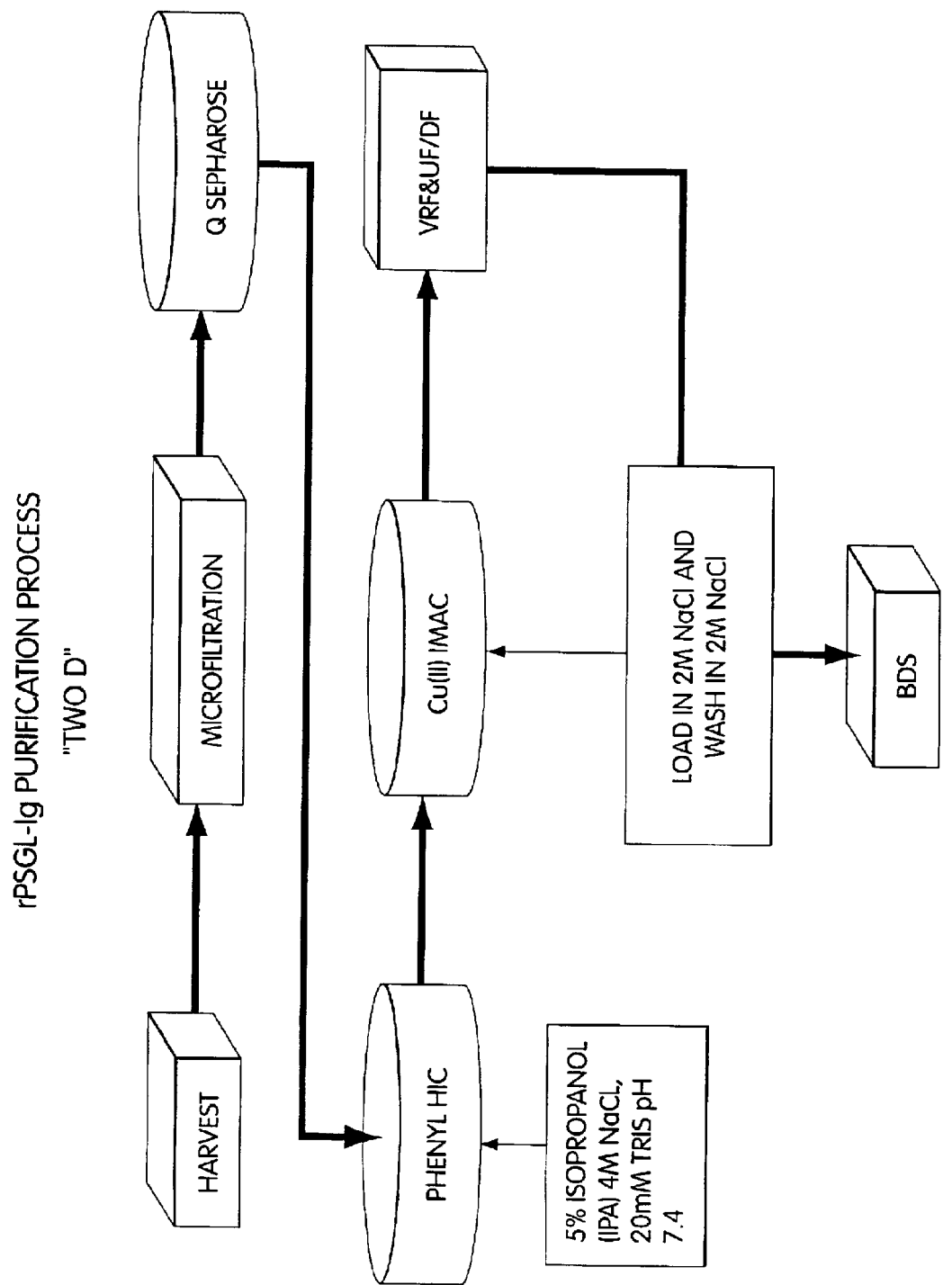
Figure 2E:
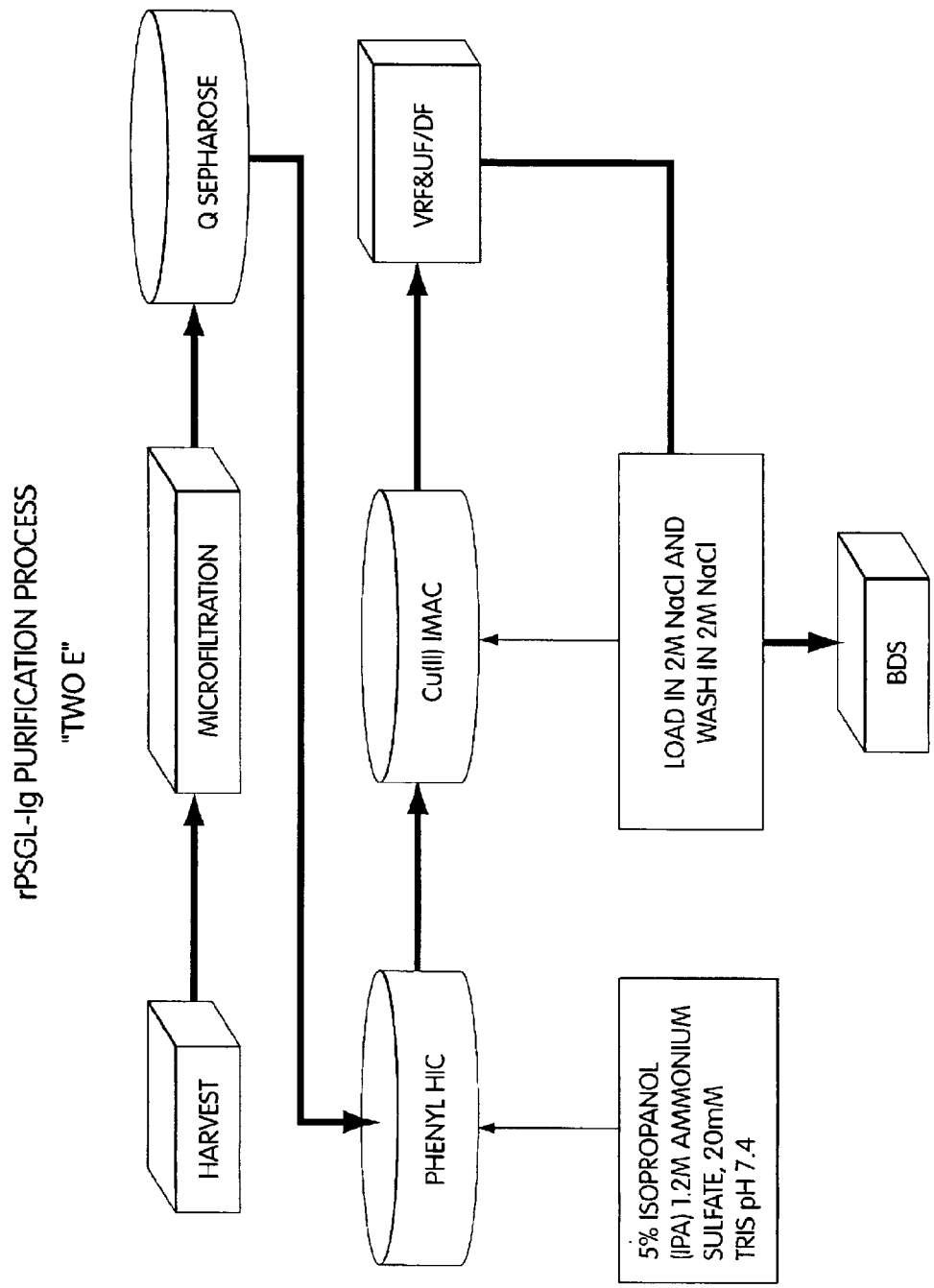
Figure 2F:
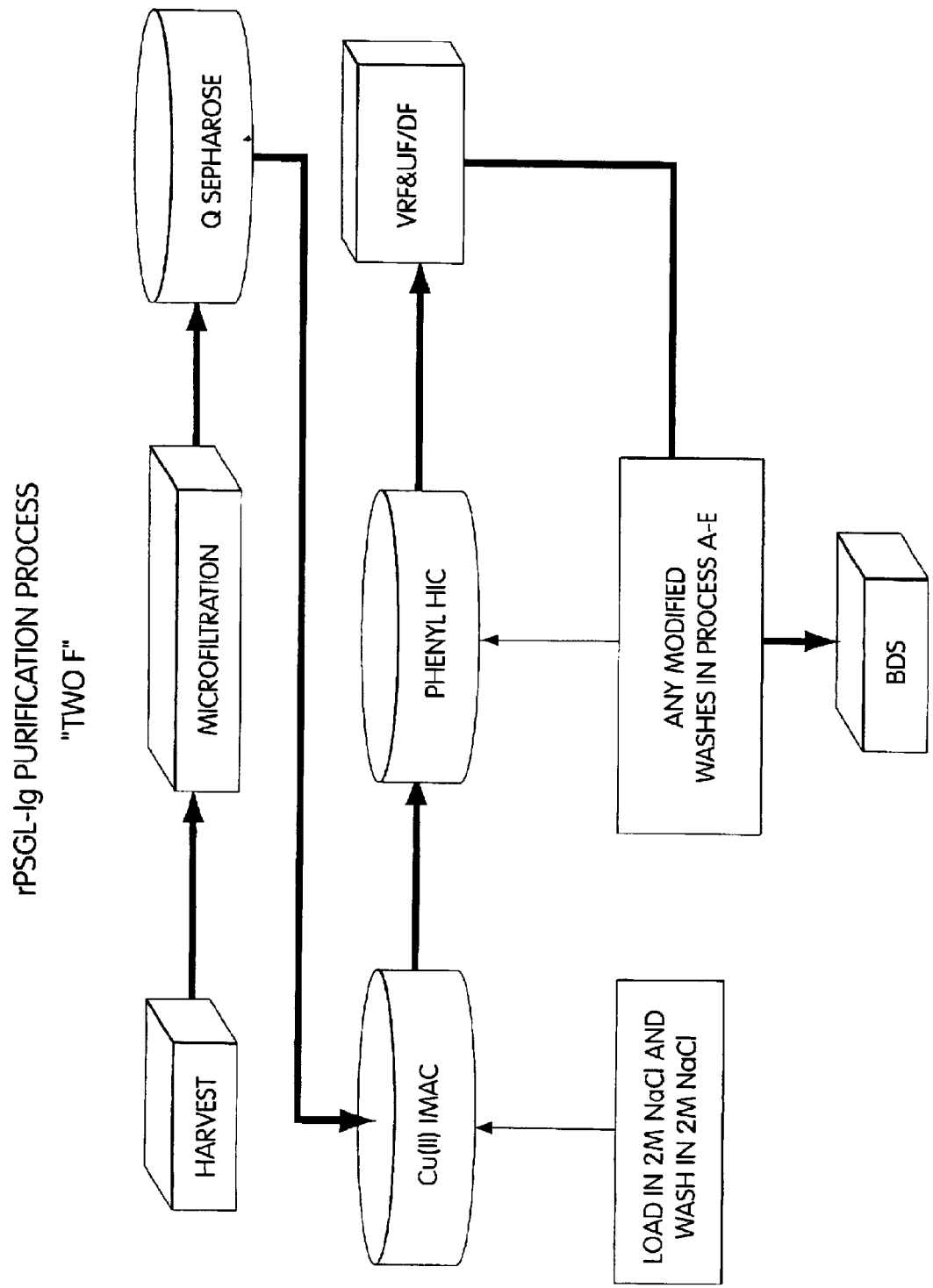
Figure 2G:
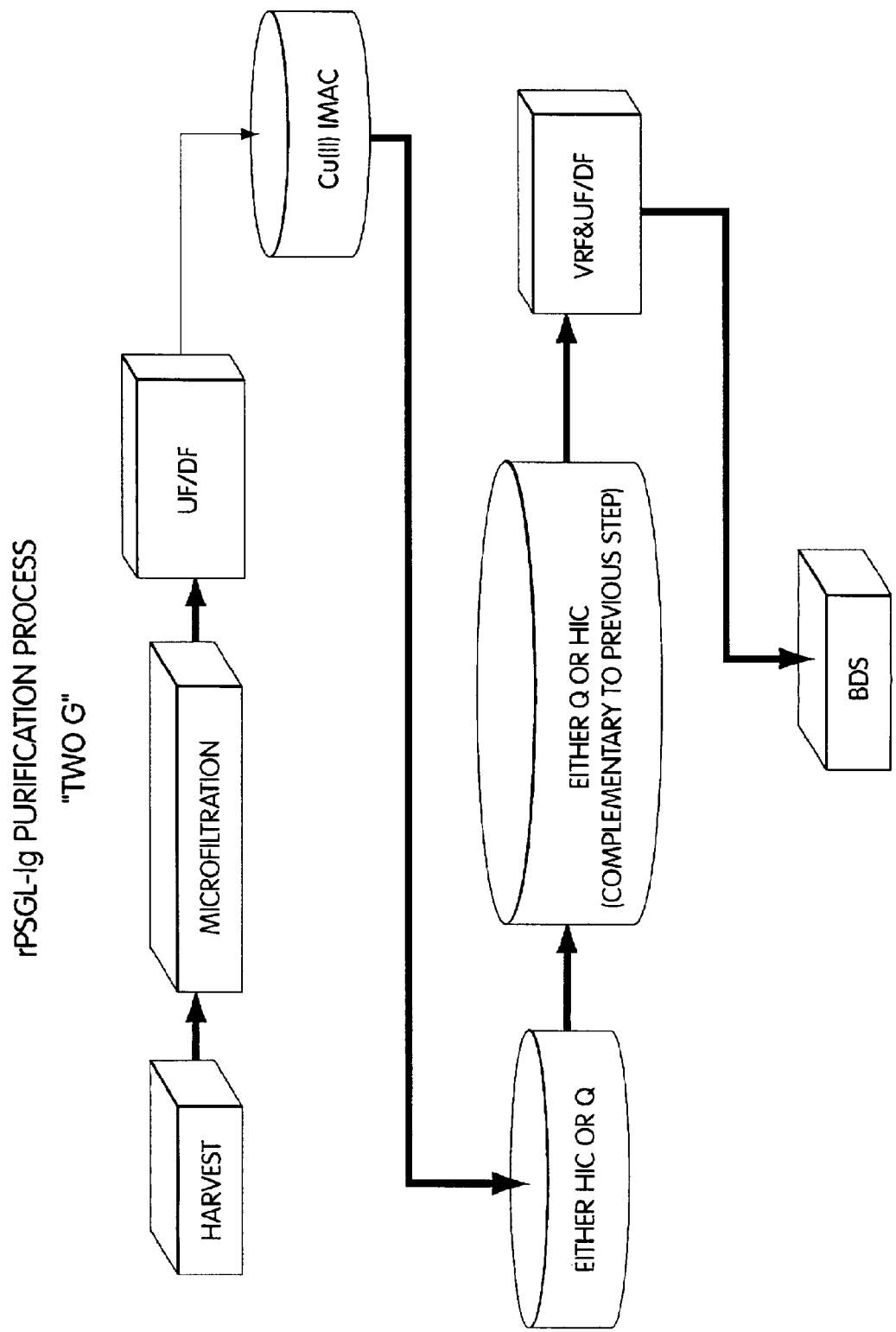

The present invention is based, at least in part, on the discovery of novel methods for purifying highly anionic target proteins and highly anionic proteins comprising an immunoglobulin domain, for example, sulfated proteins (e.g., PSGL-1). Anionic proteins are proteins having a net negative charge. Sulfated proteins are anionic proteins in which the negative charge is due to at least about one, or more preferably, five (5) or more, sulfations, e.g., at least about six (6), sulfations. Sulfations in a target protein refer to the substitution of at least one hydroxyl group (—OH) with —SO$_4$H on or between amino acid(s) contained within the target protein. Sulfations can occur, for example, at the N-terminal tyrosines as embodied in PSGL-1.

In a preferred embodiment, the sulfated protein is PSGL-1, for example, PSGL-1 comprising the amino acid set forth in U.S. Pat. No. 5,827,817, the contents of which are incorporated herein by reference, or an active portion thereof. The complete amino acid sequence of the PSGL-1 protein (i.e., the mature peptide plus the leader sequence) is characterized by the amino acid sequence set forth in U.S. Pat. No. 5,827,817 from amino acid 1 to amino acid 402, and set forth herein as SEQ ID NO:1. Hydrophobicity analysis and comparison with known cleavage patterns predict a signal sequence of 20 to 22 amino acids, i.e., amino acids 1 to 20 or amino acids 1 to 22 of PSGL-1. PSGL-1 contains a PACE (paired basic amino acid converting enzyme) cleavage site (-Arg-Asp-Arg-Arg-) at amino acid residues 38–41. The mature PSGL-1 protein is characterized by the amino acid sequence set forth in SEQ ID NO:1 from amino acid 42 to amino acid 402. A soluble form of the P-selectin ligand protein is characterized by amino acids 21 to 310 of the amino acid sequence set forth in U.S. Pat. No. 5,827,817. Another soluble form of the mature PSGL-1 protein is characterized by the amino acid sequence set forth in U.S. Pat. No. 5,827,817 from amino acid 42 to amino acid 310. The soluble form of the P-selectin ligand protein is further characterized by being soluble in aqueous solution at room temperature.

Fusion proteins of PSGL-1 (e.g., PSGL-Ig) can be made using art recognized teachings and using the teachings of U.S. Pat. No. 5,827,817, incorporated herein by reference.

PSGL-1 is a glycoprotein which may contain one or more of the following terminal carbohydrates:

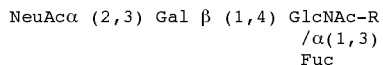

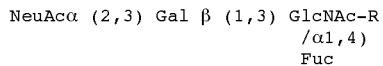

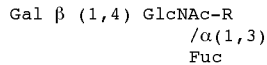

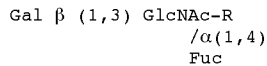

where R=the remainder of the carbohydrate chain, which is covalently attached either directly to the P-selectin ligand protein or to a lipid moiety which is covalently attached to the P-selectin ligand protein. PSGL-1 may additionally be sulfated or otherwise post-translationally modified. As expressed in COS and CHO cells, full length P-selectin ligand protein is a homodimeric protein having an apparent molecular weight of 220 kD as shown by non-reducing SDS-polyacrylamide gel electrophoresis.

The structure of the full-length PSGL-1 includes an extracellular domain (from about amino acid 21 to 310), a transmembrane domain (from about amino acid 311 to 332), and an intracellular, cytoplasmic domain (from about amino acid 333 to 402). The extracellular domain contains three consensus tripeptide sites (Asn-X-Ser/Thr) of potential N-linked glycosylation beginning at Asn residues 65, 111, and 292. The extracellular domain further contains three potential sites of tyrosine sulfation at residues 46, 48, and 51. The region comprised of residues 55–267 contains a high percentage of proline, serine, and threonine including a subdomain of fifteen decameric repeats of the ten amino acid consensus sequence Ala-Thr/Met-Glu-Ala-Gln-Thr-Thr-X-Pro/Leu-Ala/Thr, wherein X can be either Pro, Ala, Gln, Glu, or Arg. Regions such as these are characteristic of highly O-glycosylated proteins.

Substantial deletions of the PSGL-1 sequence can be made while retaining P-selectin ligand protein activity. For example, PSGL-1 comprising the sequence from amino acid 42 to amino acid 189, the sequence from amino acid 42 to amino acid 118, or the sequence from amino acid 42 to amino acid 89 of SEQ ID NO:1 each retain the P-selectin protein binding activity and the ability to bind to E-selectin. PSGL-1 proteins in which one or more N-linked glycosylation sites (such as those at amino acids 65, 111 and 292) have been changed to other amino acids or deleted also retain P-selectin protein binding activity and the ability to bind E-selectin. P-selectin ligand proteins comprising from amino acid 42 to amino acid 60 (which includes a highly anionic region of the protein from amino acid 45 to amino acid 58) also retain P-selectin ligand protein activity; however, P-selectin ligand proteins limited to such sequence do not bind to E-selectin. Preferably, a P-selectin ligand protein retains at least one (more preferably at least two and most preferably all three) of the tyrosine residues found at amino acids 46, 48 and 51, sulfation of which may contribute to P-selectin ligand protein activity.

This invention is further illustrated by the following examples which should not be construed as limiting. The contents of all references, patents and published patent applications cited throughout this application, as well as the Figures, and Appendix A are incorporated herein by reference. All references to the amino acid sequence of PSGL-1 are based on the amino acid sequence of PSGL-1 set forth in U.S. Pat. No. 5,827,817 and set forth herein as SEQ ID NO:1.

EXAMPLES

Methods: General methods for purifying proteins are found in Janson, J. C. and L. Ryden (eds.) *Protein Purification: Principles, High Resolution Methods and Applications.* VCH Publishers, Inc. New York (1989), U.S. Pat. No. 5,429,746, entitled Antibody Purification, and U.S. Pat. No. 5,115,101, entitled Removal of Protein from Antibody Preparations, the contents of which are incorporated herein by reference.

Example 1

Purification of Recombinant PSGL-Ig Fusion Protein—Process I

This example describes the purification of a recombinant PSGL-Ig fusion protein by column chromatography (FIG. 1).

A soluble P-selectin ligand protein was expressed in CHO cells and the conditioned media was harvested for protein purification. A Q Sepharose™ Fast Flow (Amersham Pharmacia) column with an 8 cm bed depth was prepared according to the manufacturer's instructions. The column capacity for PSGL in conditioned media is approximately 1 mg PSGL/ml resin.

Anion exchange chromatography was performed as follows. Microfiltered CHO conditioned media was loaded onto the column at approximately pH 7, conductivity below 20 mS/cm. The column was washed with 20 mM histidine, 400 mM NaCl, pH 6.5 to remove hyposulfated rPSGL-Ig, e.g., 4 or less sulfations. The loading and washing steps were performed at 3.5 cm/minute. The column was eluted at pH 6.5 with 1M NaCl, 20 mM histidine, pH 6.5 at <1.1 cm/minute. The pH of this step could be between pH 4 and 8, but is preferably pH 6.5. The eluted peak contains PSGL-Ig, DNA, and histones as well as other contaminates. The Q column binds DNA, and the histones are attached to the DNA. The PSGL elution (caused by raising the salt concentration) coincides with the DNA elution. The purity of PSGL-Ig is >80%. Only 50% of the DNA is removed by this step.

Under these conditions, hypersulfated rPSGL-Ig molecules, e.g., five or six sulfations, are preferentially purified. Active rPSGL-Ig ideally has five or six sulfations on the N-terminal tyrosines.

The eluent from the anion exchange column was further purified using a hydrophobic interaction chromatography (HIC) column as follows.

A Phenyl Toyopearl 650C column (Rohm and Haas) with a 9 cm bed depth was prepared according to the manufacturer's instructions. The capacity of the HIC column is approximately 3.5 mg PSGL/mL resin. The column was equilibrated in 1.2M ammonium sulfate, 20 mM Tris, pH 7.4 at ≦1.3 cm/minute. The eluent from the Q Sepharose column was adjusted to 1.2M ammonium sulfate, 20 mM Tris, pH 7.4 by adding 3M ammonium sulfate, 50 mM Tris, pH 7.4, and loaded onto the HIC. Alternatively, the load could be done in 4M NaCl rather than 1.2M Ammonium sulfate. The column was washed with 1.2M ammonium sulfate, 20 mM Tris pH 7.4. Both the loading and washing steps were performed at a rate of approximately 1.3 cm/minute. The HIC column was eluted with 0.48M ammonium sulfate, 20 mM Tris, pH 7.4 at 0.65 cm/minute. Under these conditions, the HIC column removes primarily H2A and H2B histones which do not bind DNA as tightly as H3 and H4 histones. H2 histones appear in the wash fraction, and the peak contains H3 and H4 histones, and some H2 histones. In addition, a large plurality of the DNA stays on the histones and elutes in the peak. The product is >95% pure of contaminating proteins, and 85% of the DNA is removed by this step.

The eluent from the HIC column was further purified using a metal chelate chromatography (IMAC) column as follows.

An IMAC Copper (II) column on Fractogel Chelate (M) (E. Merck) was prepared according to the manufacturer's instructions. The IMAC column had a bed depth 6.4–7.2 cm, and a capacity of approximately 6.6 mg PSGL/mL resin.

The column was equilibrated with 50 mM potassium phosphate ($KPO_4$), 2.0M NaCl, 2 mM imidazole, pH 7 for 5 cv at ≦5 cm/minute. The eluent from the HIC column was adjusted to 2 mM imidazole, 50 mM KPO4, pH 7 200 mM NaCl and loaded onto the IMAC column. The column was first washed with equilibration buffer, and then washed with 40 mM MES, 1M NaCl, 5 mM imidazole, pH 6.6 at ≦5 cm/minute. This low salt concentration does not break up the histone/DNA complex on the IMAC column. The column was eluted with 40 mM MES, 1M NaCl, 35 mM imidazole pH 6.6. The IMAC column removes primarily H3 and H4 histones. H3 and H4 histones, and some H2, are in the strip, although some H3 and H2 histones are found in the IMAC peak. The resulting product is >99.9% pure of contaminating proteins, and this step removes 95% of the DNA. Overall, there is approximately 2.5 LRV of DNA clearance from this whole process.

This process allowed DNA to be carried through the entire process train, as the DNA bound directly to the Q column. In the Q step the DNA also bound to histones (e.g., H2A, H2B, H3, and H4) which are naturally occurring DNA binding proteins which are present in our load to the Q column. On the Q column, therefore, there was a sandwich, in which the DNA bound to the Q column and the histones bound to the DNA. In the subsequent steps, the sandwich was reversed, as DNA does not bind to the HIC or the IMAC column directly. Instead, the histones bound to the HIC or IMAC column, and the DNA bound to the histones. When the histones elute from the HIC or IMAC, they carry the DNA contamination with them. Poor DNA removal due to DNA/protein interactions may be often encountered in protein purification, especially in the case of highly anionic target proteins, and especially where these anionic proteins are eluted from an anion exchange column.

Example 2

Purification of Recombinant PSGL-Ig Fusion Protein—Process II

This example describes the purification of a recombinant PSGL-Ig fusion protein (rPSGL-Ig) by column chromatography, including the step of dissociating the contaminating histone/DNA complexes with either salt or an alcohol, thereby increasing the purity of the PSGL-Ig proteins (FIG. 2).

An anion exchange chromatography step on Q Sepharose was performed as described in Example 1.

The eluent from the anion exchange column was further purified using a hydrophobic interaction chromatography (HIC) column as follows. A Phenyl Toyopearl 650C column (Rohm and Haas) with a 9 cm bed depth was prepared according to the manufacturer's instructions, and equilibrated in 1.2M ammonium sulfate, 20 mM Tris, pH 7.4. The pH of this step could be between 6–8, but is preferably pH 7.4.

The Q peak was adjusted to 1.2M ammonium sulfate, 20 mM Tris, pH 7.4 by adding 3M ammonium sulfate, 50 mM Tris pH 7.4 and loaded onto the column. Alternatively, the load could be done in 4M NaCl rather than 1.2M ammonium sulfate. The column was washed with 1.2M Ammonium Sulfate, 20 mM Tris pH 7.4, followed by washing with 4M NaCl, 20 mM Tris, pH 7.4. Washing with 4M NaCl removes 90% (or 1 $\log_{10}$ removal or 1 LRV) of the DNA from the column. Alternatively, one could wash with 5% isopropanol and 1.2M Ammonium Sulfate. This removes 99.9% of the DNA from the column ("3 $\log_{10}$ removal", or 3 LRV). Alternatively one could wash with 5% ethanol and 1.2M Ammonium Sulfate. This removes 99.9% of the DNA from the column ("3 $\log_{10}$ removal", or 3 LRV). Alternatively one could wash with one could wash with 5% ethanol and 4M NaCl. This removes 99.9% of the DNA from the column ("3 $\log_{10}$ removal", or 3 LRV). Alternatively one could wash with 5% isopropanol and 4M NaCl. This removes 99.9% of the DNA from the column ("3 $\log_{10}$ removal", or 3 LRV). The loading and washing steps were performed at a rate of approximately 1.3 cm/minute. The column was then eluted with 0.48M Ammonium Sulfate, 20 mM Tris, pH 7.4 at a rate of 0.65 cm/minute.

As before, this HIC with these conditions removes primarily H2A and H2B histones, which do not bind DNA as tightly as the H3 and H4 histones. H2 histones appear in the wash. The peak contains H3 and H4, with some H2 histones. However, we have found that by washing with higher salt concentrations, the DNA/histone interaction can be broken up. Thus by washing with, for instance, 4M NaCl rather than 1.2M ammonium sulfate, the DNA breaks off from the histone, and comes off in the wash. Under these conditions, a large plurality of the DNA comes off in the wash, and the histones still elute in the peak. This HIC step could alternatively be run after the IMAC step (see below). This could result in 99.9% more DNA being removed (3 LRV).

The eluent from the HIC column was further purified using a metal chelate chromatography (IMAC) column as follows.

An IMAC Copper (II) column on Fractogel Chelate (M) (E. Merck) was prepared according to the manufacturer's instructions. The IMAC column had a bed depth 6.4–7.2 cm, and a capacity of approximately 6.6 mg PSGL/mL resin. The pH of this step can be between 4.8 and 8, but is preferably pH 6.6.

The column was equilibrated with 50 mM potassium phosphate ($KPO_4$), 2.0M NaCl, 2 mM imidazole, pH 7 for 5 cv at $\leq 5$ cm/minute. Alternatively, the column can be equilibrated at 200 mM NaCl rather than 2M NaCl. The eluent from the HIC column was adjusted to 2 mM imidazole, 50 mM KPO4, pH 7, 200 mM NaCl and loaded onto the IMAC column. The load can alternatively be run at 200 mM NaCl rather than 2M NaCl.

The column was first washed with equilibration buffer, and then washed with 40 mM MES, 2M NaCl, 5 mM Imidazole, pH 6.6 at $\leq 5$ cm/minute. The column was eluted with 40 mM MES, 1M NaCl, 35 mM imidazole pH 6.6. The IMAC column removes primarily H3 and H4 histones. These histones, and some H2 histones, are in the strip. Some H3 and H2 histones are also found in the IMAC peak.

This step removes 90% more DNA than the process I step of Example 1 (1 LRV) using either the high salt load or the high salt wash. The novelty of this step is to load with 2M NaCl or to wash with 2M NaCl to remove the DNA from the histones/DNA complex. The histones stick to the IMAC column, and the DNA sticks to the histones. Since the DNA binds better to the H3/H4 complex than to the H3/H2 or to simply the H2 complex, removing the H3/H4 complex as soon in the process as possible would be beneficial. Thus running the HIC after the IMAC has shown that more DNA clearance can be achieved (99.9% more clearance or 3 LRV). Therefore putting the IMAC as early in the process as possible could conceivably result in a further reduction of DNA. IMAC as the first step, however, would require an ultrafiltration/diafiltration to remove small molecular weight amino acids and other amine containing groups from the load.

Example 3

Purification of Recombinant PSGL-Ig Fusion Protein—Process III

Figure 3:
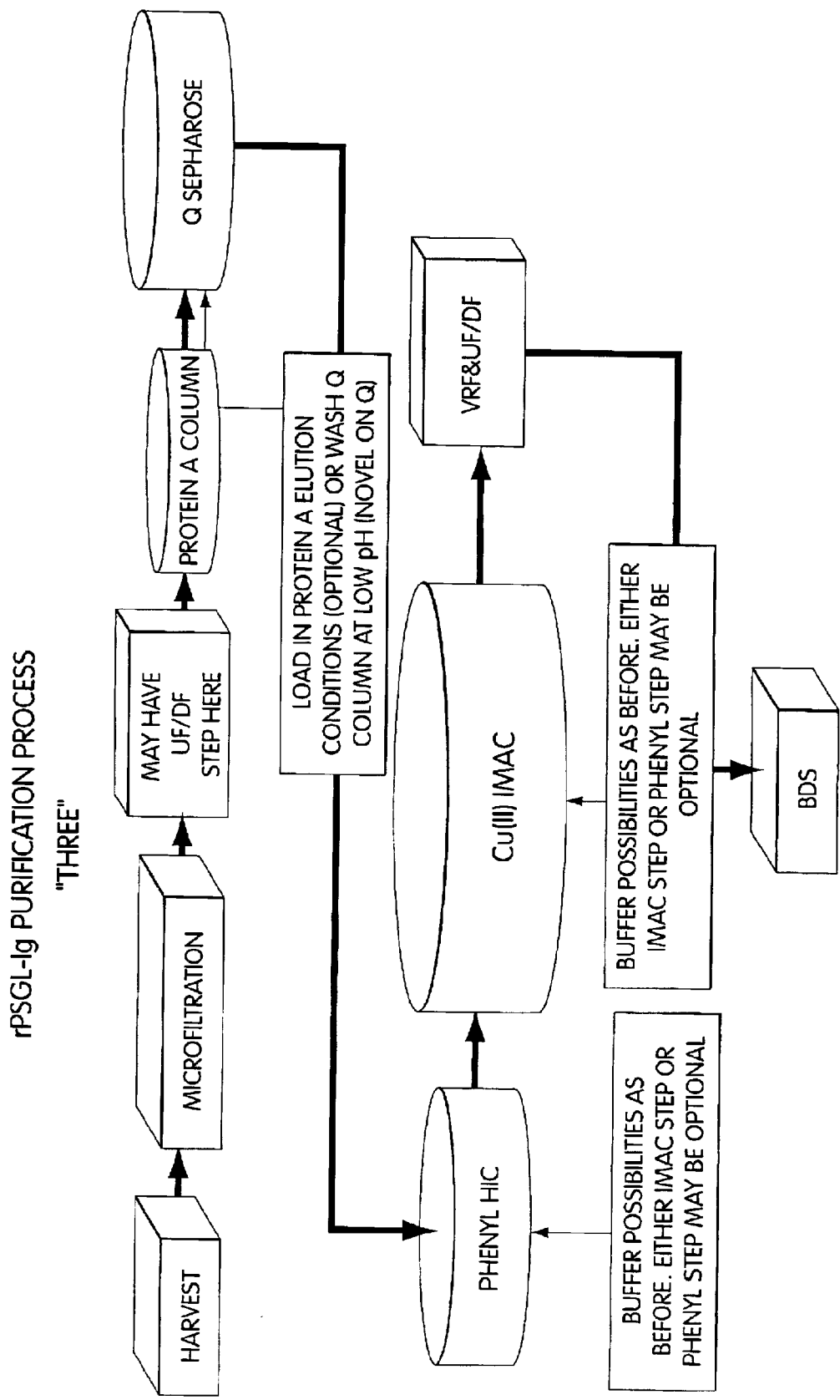

This example describes an alternative method for the purification of a recombinant PSGL-Ig fusion protein by column chromatography. In contrast to the purification scheme described in Example 1, this process uses an affinity step as the first purification step (FIG. 3). The affinity purification step uses Protein A which binds the Fc portion of the rPSGL-Ig chimera. The rPSGL-Ig is eluted from the Protein A column at low pH, in this case pH of 3.7. The Protein A step gives better clearance if the column is washed with 1M NaCl after loading. This concentration of salt is higher than that typically used (usually about 150 mM NaCl), and thus is novel. The clearance of DNA from this step goes from 4 $\log_{10}$ removal value (LRV) to 6 LRV with the addition of this salt step. This represents a 100 fold increase in removal of DNA.

The Protein A step does not appear to bind histones, and gives good DNA clearance. Thus, histones are not noticeably present in the steps following the Protein A step. However, since the Protein A leaches from the Protein A column, the subsequent steps are performed to remove the Protein A. The most novel method for removing the leached Protein A is to load the Protein A eluate directly on the Q column, either at neutral or at low pH, or to wash the Q column at low pH. Q columns are not normally run at low pH, especially not pH 4. Thus the capture of the rPSGL-Ig directly from the Protein A eluate or the washing of the Q column at low pH, or a combination thereof, is novel. Since the rPSGL-Ig and the Protein A are at low pH, a large plurality of the rPSGL-Ig is not bound to the leached Protein A. As a result, the Protein A does not bind to the Q column, but is found in the Q flow through. This is also novel. Thus, the Q column is being used to remove Protein A.

A Protein A Fast Flow column (Amersham Pharmacia) with a bed depth of 6–10 cm is prepared according to the manufacturer's instructions. The column capacity is approximately 1 mg/mL to 6 mg/mL. The column is equilibrated with 20 mM Tris, 200 mM NaCl, pH 7.2 to 8, preferably pH 7.4. Microfiltered conditioned media is loaded onto the column between pH 7 and pH 8, preferably pH 7.4, at approximately 30–300 cm/hour, preferably 150 cm/hour. The column is washed with 20 mM Tris, 200 mM NaCl, pH 7 to 8, preferably pH 7.4, and eluted with 20 mM citrate, pH 3 to 4, preferably pH 3.7, at 50–300 cm/hour. The purity is >95% for proteins, and >99% of the DNA is removed by this step.

The eluent from the Protein A column is further purified on a Q Sepharose™ Fast Flow column (Amersham Pharmacia) with an 8 cm bed depth. The capacity of the Q Sepharose column for PSGL at pH 3.6 to 4.0, preferably about pH 3.8, after the Protein A step is approximately ≦6 mg PSGL/mL resin.

The Protein A peak is loaded directly onto the Q Sepharose column without adjusting the pH, or the peak is neutralized prior to loading onto the Q Sepharose column. In either case, the column is washed with 200 mM NaCl and 20 mM citrate at pH 3.5 to 4, preferably about pH 3.8, to remove residual Protein A. Both methods remove leached Protein A, hyposulfated rPSGL-Ig, N-terminally clipped rPSGL-Ig, and pro-rPSGL-Ig (a precursor species to rPSGL-Ig that does not have enzymatic cleavage of the N-terminus).

Following the pH 3.5 to 4 wash, the column could be washed with 20 mM Histidine, 400 mM NaCl, pH 6.5 to remove hyposulfated rPSGL-Ig. Hyposulfated rPSGL-Ig molecules have 4 or less sulfations, whereas active rPSGL-Ig ideally has 5 or 6 sulfations on the N-terminal tyrosines. The column loading and washing steps are performed at a rate of 3.5 cm/minute. The column is eluted at pH 6.5 with 1M NaCl, 20 mM histidine, pH 6.5. Alternatively, one could elute at pH 3.5 to 4.0 preferably about 3.8 in 500 mM NaCl, 20 mM citrate at <1.1 cm/minute. Proteins represent <2% of the peak.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method for purifying a protein in a sample from a plurality of DNA/histone complexes, comprising a step of loading the sample containing the protein on a metal chelate chromatography substrate wherein the protein is captured on the substrate, and a step of washing the substrate, wherein at least one of the loading step and the washing step uses a solution comprising at least about 2M NaCl to remove DNA from the sample, thereby purifying the protein in the sample.

2. The method of claim 1, wherein the protein is highly anionic.

3. The method of claim 2, wherein the protein is hypersulfated.

4. The method of claim 3, wherein the protein is PSGL-1.

5. The method of claim 1, wherein the loading step uses the solution comprising at least about 2M NaCl to remove DNA from the sample.

6. The method of claim 1, wherein the washing step uses the solution comprising at least about 2M NaCl to remove DNA from the sample.

7. A method for purifying a protein in a sample from a plurality of DNA/histone complexes, comprising a step of loading the sample containing the protein on a metal chelate chromatography substrate wherein the protein is captured on the substrate, and a step of washing the substrate, wherein at least one of the loading step and the washing step uses a solution comprising an ionic strength of at least about 2M to remove DNA from the sample, thereby purifying the protein in the sample.

8. The method of claim 7, wherein the protein is highly anionic.

9. The method of claim 8, wherein the protein is hypersulfated.

10. The method of claim 9, wherein the protein is PSGL-1.

11. A method for purifying a highly anionic protein in a sample from a plurality of DNA/histone complexes, comprising a step of loading the sample containing the protein on a hydrophobic interaction chromatography substrate wherein the protein is captured on the substrate, and a step of washing the substrate, wherein the washing step uses a solution comprising either at least about 5% ethanol or at least about 5% isopropanol to remove DNA from the sample, thereby purifying the protein in the sample.

12. The method of claim 11, wherein the protein is hypersulfated.

13. The method of claim 12, wherein the protein is PSGL-1.

* * * * *